United States Patent [19]

Nagel

[11] 4,066,071

[45] Jan. 3, 1978

[54] EXTENSION PULL THROUGH DEVICE TO ALLOW FOR EASIER PASSAGE OF FLEXIBLE FIBER ENDOSCOPE

[76] Inventor: John G. Nagel, 200 Closter Dock Road, Closter, N.J. 07624

[21] Appl. No.: 604,999

[22] Filed: Aug. 15, 1975

[51] Int. Cl.² .............................................. A61B 1/06
[52] U.S. Cl. ....................................... 128/7; 128/2 M; 128/DIG. 9
[58] Field of Search ........................................ 128/3–8, 128/214.4, 243, 266, 348–350, DIG. 9, 2 M, 7; 15/104.3

[56] References Cited

U.S. PATENT DOCUMENTS

| | | | |
|---|---|---|---|
| 2,961,675 | 11/1960 | Stickney | 15/104.3 |
| 3,090,378 | 5/1963 | Sheldon et al. | 128/4 |
| 3,091,235 | 5/1963 | Richards | 128/6 |
| 3,329,074 | 7/1967 | Gosselin | 95/11 |
| 3,572,325 | 3/1971 | Bazell et al. | 128/6 |
| 3,788,303 | 1/1974 | Hall | 128/4 |
| 3,788,304 | 1/1974 | Takahashi | 128/6 |
| 3,822,697 | 7/1974 | Komiya | 128/3 |
| 3,895,637 | 7/1975 | Choy | 128/348 |
| 3,913,568 | 10/1975 | Carpenter | 128/11 |

*Primary Examiner*—John D. Yasko
*Assistant Examiner*—Henry S. Layton
*Attorney, Agent, or Firm*—Pennie & Edmonds

[57] ABSTRACT

A flexible endoscope having a fiber bundle for transmitting optical images from a distal end where an object to be viewed is located to a proximal end where an image of the object can be viewed by an operator. The endoscope incorporates a mechanism for advancing the endoscope toward the object to be viewed.

33 Claims, 12 Drawing Figures

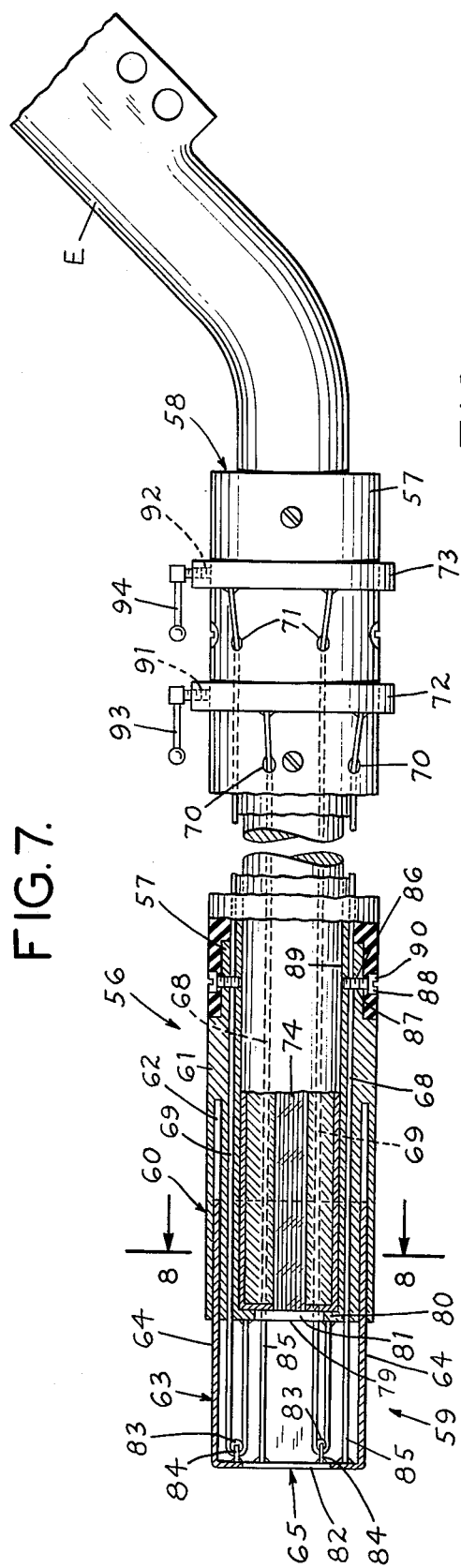
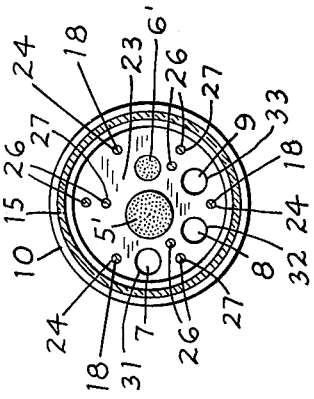

EXTENSION PULL THROUGH DEVICE TO ALLOW FOR EASIER PASSAGE OF FLEXIBLE FIBER ENDOSCOPE

BACKGROUND OF THE INVENTION

Endoscopes are used for viewing ordinarily inaccessible sites such as internal organs of the human body. These devices are normally characterized by a flexible enlongated tube having a distal end for insertion into a passage leading to the object to be viewed and a proximal end at which an operator may view an image of the object. Images may be transmitted from the distal end to the proximal end of the tube by means of flexible bundles of translucent fibers, commonly called fiber optics. The use of such a fiber bundle allows the flexible tube of an endoscope to conform to the undulations of the passage leading to the area being viewed while forming at the proximal end and undistorted image of the object being viewed.

Normally, the distal end of the endoscope is inserted into the passage and advanced toward the site of the object to be viewed by grasping the emergent portion of the endoscope and simply pushing it inward. Where the passage is unusually tortuous or has a configuration which otherwise offers significant resistance to the endoscope traversing the passage, inward movement often cannot be achieved by pushing on the emergent portion of the flexible tube without causing severe pain to the patient. This pain is symptomatic of the force exerted on the walls of the passage by the flexible endoscope tube as it tends to bend laterally when the effort the operator exerts to advance the endoscope along the passage is opposed at the distal end.

Workers in the art have sought to alleviate the problem by various means. Efforts have been made to reduce the resistance to inward motion of the endoscope by enlarging the passage ahead of the distal end with the aid of compressed air which can be delivered to the distal end through a small hose built into the endoscope. This technique is difficult to use, for air pressure which is sufficient to enlarge the passage to a useful degree is generally great enough to at least cause pain and it may even be dangerous to the patient.

Various mechanical devices have been proposed for incorporation in an endoscope to aid its movement within the passage leading to the object to be viewed. Some of these devices have sought to guide an endoscope along a tortuous passage by means of cables connected to the distal end of the endoscope and controlled from the proximal end. Examples of such devices are disclosed in U.S. Pat. to Stickney, No. 2,961,495; Richards, No. 3,091,235; Bazell, No. 3,572,325 and Hall, No. 3,788,303.

It has also been proposed to move one component of an endoscope relative to another component by means of control cables extending from the proximal end to the distal end. For example, cables extending along the endoscope have also been used to move one or more lenses toward and away from the distal end of the bundle of fibers. Such a device is disclosed in the U.S. Pat. No. 3,090,378 to Sheldon et al. However, these techniques and devices of the prior art are of little or no aid in moving an endoscope inwardly along a tortuous passage to a site to be observed.

SUMMARY OF THE INVENTION

The present invention provides means for tractively moving the main body of a flexible endoscope along a tortuous passage and thereby eliminating one source of pain and discomfort in endoscopic examinations and procedures. Embodiments of my invention may be made compatible with most endoscopic apparatus and accessories. They may be designed as integral parts of endoscopes or they may be designed as accessories to be attached to endoscopes of existing design.

According to my invention, I provide means at the distal end of the main flexible body of an endoscope, but operable from the a proximal end, by which a pilot section of the endoscope is advanced along the passage for a short distance ahead of the flexible main body. The pilot section is then held fixed relative to the subject under examination and serves as an anchor site from which tractive effort is exerted on the main body of the endoscope to pull it further inward along the passage. This sequence of operations is repeated until the distal end of the endoscope arrives at the site of interest. Thus, the main body of the device is effectively kedged along the tortuous passage, thereby eliminating the difficult and painful procedure of inserting the endoscope in the patient by pushing on an emergent portion of the main body.

A preferred embodiment includes a pilot section in the form of a rigid frame structure which is mounted on a rigid portion at the distal end of the main body. The pilot section is free to move longitudinally of the rigid portion of the body. The pilot section is connected to one or more push rods or wires which extend through passages in the endoscope to the proximal end of the main body, where they are accessible to the operator and where they can be pushed foward to move the pilot section inward relative to and ahead of the rigid portion. Means are provided adjacent the proximal end of the main body for releasably fixing the push rods or wires so that through them the pilot sections may be fixed in position relative to the patient after it is advanced along the passage. Pull cables are also provided for drawing the main body along the passage after the pilot section has been fixed in place ahead of the main body by the push rods or wires. One end of each pull cable is fixed to the distal end of the main body. From there the cable is led to and cooperates with direction reversing means, such as a pulley, attached to the pilot section and then led back through a passage in the main body to a position adjacent the proximal end where it is brought out to be accessible to the operator.

DESCRIPTION OF THE DRAWINGS

FIG. 6 is a sectional view taken along lines 6—6 of FIG. 3.

FIG. 7 shows another embodiment of the invention secured to a standard endoscope.

FIG. 8 is a sectional view taken along lines 8—8 of FIG. 7.

DETAILED DESCRIPTION OF THE PREFERRED EMBODIMENTS

Figure 1:
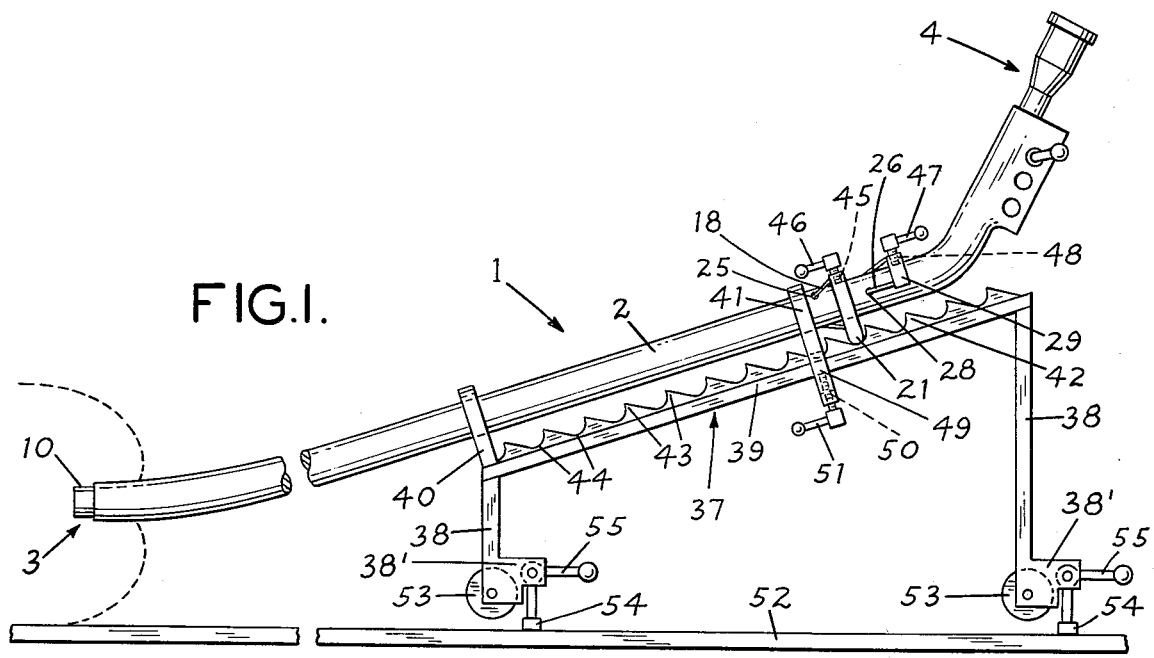
FIG. 1 shows a perspective view of an endoscope on a frame.
Figure 2:
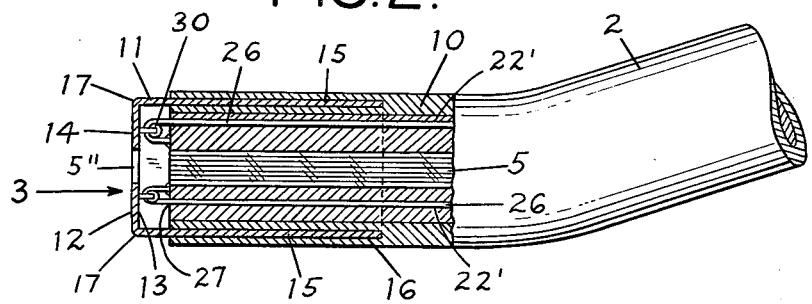
FIG. 2 is a sectional view of the distal end of the endoscope showing the tractive mechanism in a closed position.

As shown in FIG. 1, the main body of an endoscope 1 has a flexible outer sheath 2 which may contain various optical elements and control devices to enable an operator to view sites within a patient and to perform certain procedures at the site. The endoscope 1 has a distal end 3 for insertion into the passage or duct leading to the site to be viewed and a proximal end 4 at which the operator may view an image of the site and manipulate the control devices. A flexible bundle 5 of optical fibers extends the length of the endoscope and transmits the image from the face of the distal end to the face at the proximal end. Another bundle 6 of optical fibers extends the entire length of the endoscope and transmits light from a source at the proximal end 4 to the distal end 3 to provide light for viewing the remote site with the source itself always outside the patient. Replacement of the source can be done readily without interrupting a procedure. Within the sheath there are also provided a water tube 7, a biopsy tube 8 and an air tube 9 each connected to its respective source of water, air and a biopsy mechanism. With these devices, once the distal end of the endoscope has reached the intended site, that area can be cleansed, dried or a biopsy taken as desired by operation or controls at the proximal end of the endoscope. This much of the structure of an endoscope is well known in the art.

In this illustrative embodiment of my invention, at the distal end 3 of the main body there is a relatively short rigid portion 10 within which there is a longitudinally extending annular cavity 16 coaxial with the rigid portion. A pilot section 11, having rigid cylindrical wall 15 and an end wall 12 is received within the annular cavity 16 in telescoping relation to the rigid portion 10. The end wall 12 is provided with one or more suitably positioned apertures 5", 6" through which light may pass to and from the site to be observed and, apertures 34, 35, 36 through which any accessory devices may operate at the site. The juncture 17 of the cylindrical wall 15 and the end wall 12 is provided with a smooth radius to permit the pilot section to advance through the passage to the site without damaging the walls of the passage.

As shown in FIGS. 3 through 6, means are provided for extending the pilot section 11 outwardly ahead of the rigid portion 10 of the main body. This means comprises one or more, in this case three, push rods or wires 18. These are formed of materials which are sufficiently flexible to conform to the convolutions of the main body of the endoscope as it assumes the configuration of the passage of the site, but the material is also sufficiently inflexible so that short, laterally unsupported lengths do not bend when subjected to the compressive forces which one skilled in the art would expect to be applied in a given design. Piano wire is an example of such material.

At the distal end of the main body, the push rods or wires are fixed to the inner surface of the end wall 12 and extend through passages 22 through the main body to the proximal end where they emerge and are attached to push ring 21.

Figure 3:
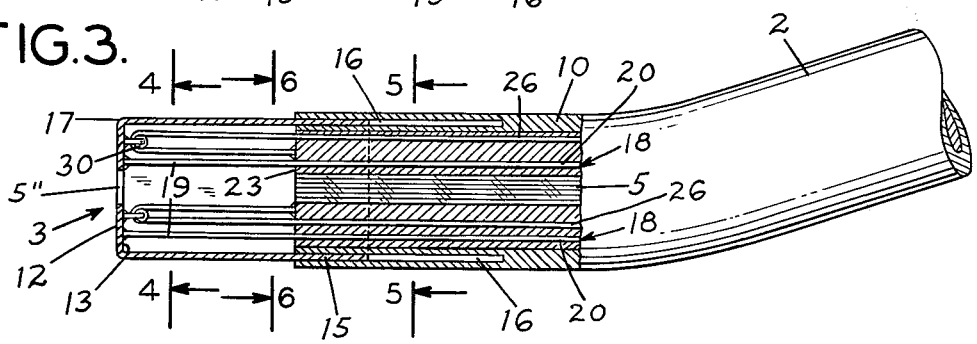
FIG. 3 is a section view showing the tractive mechanism of FIG. 2 in an extended position.
Figure 4:
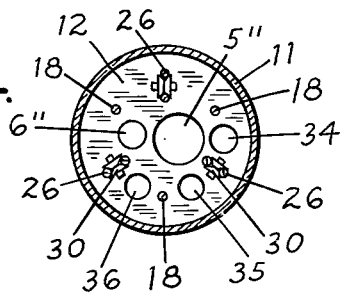
FIG. 4 is a sectional view taken along lines 4—4 of FIG. 3.
Figure 5:
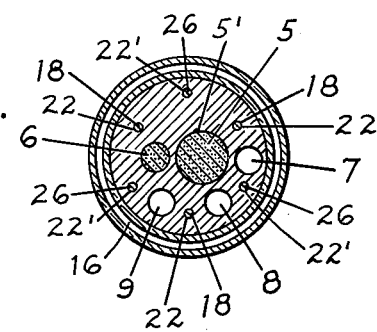
FIG. 5 is a sectional view taken along lines 5—5 of FIG. 3.

In the alternative, cables with flexible sheaths may be used. Each may have a rigid portion 19 and a flexible portion 20. Rigid portion 19 is approximately the same length as the rigid portion 10 of the endoscope with the flexible portion 20 extending the remaining distance to the proximal end of the endoscope where it is fixed to the push ring 21. The push cables 18 extend through passages 22, which are slightly larger in diameter than cables 18, substantially the entire length of the endoscope. At the distal end 3 passages 22 emerge at face 23 of rigid portion 10 defining openings 24 therein, as seen in FIG. 6, and at the proximate end emerge at openings 25 in sheath 2 as shown in FIG. 1. With this configuration the cables can be moved longitudinally along the length of the endoscope through passages 22. The operator can control the forward movement of the pilot section 11 by merely pushing the ring 21. The push cables 18 will move forward through the passage 22 causing the pilot section 11 also to move forward to an extended position as shown in FIG. 3 relative to the rigid portion 10. The rigid wire 19 insures during forward movement of push cable 18 that that portion of the cable beyond the face 23 will not buckle to prevent the forward motion of cable 18 from being transferred to pilot section 11.

Means are also provided for drawing the main body of the endoscope toward the pilot section when the latter has been extended by the push rods or wires. These are pull cables 26 which extend the entire length of the endoscope through passages 22' from the distal end 3 to the proximal end 4. The passages 22' emerges at the face 23 of the rigid portion 10 defining therein openings 27, and the proximal end the passages 22' emerge through sheath 2 at openings 28 at some distance behind the push ring 21. This arrangement allows both the pull cables 26 and push cables 18 to be moved relative to the passages 22 and 22' in sheath 2 regardless of the undulations in the endoscope.

At the proximal end 4 the pull cables 26 are fixedly attached to a pull ring 29. At the distal end each pull cable 26 extends out of the passage 22' through opening 27 where it is reeved through a pulley 30 and then secured to the main body of the endoscope. Each pulley 30 is secured to the inner surface 13 of the pilot section 11. With the pilot section 11 in its extended position, the pull cables allow the main body of the endoscope to be drawn toward the pilot section 11 by merely pulling the cables 26 at the proximal end 4.

Alternate operation of the push ring and pull ring as described will advance the endoscope along the passage provided the pilot section can be made to remain stationary relative to the passage after the pilot section is advanced by the push rods. The friction between the walls of the passage and the pilot section 11 may be sufficient to anchor the pilot section 11 in position while the endoscope is advanced by the tractive force exerted on the pull cables. Where this friction is insufficient a detent frame 37 can be used to insure that the pilot section 11 is not simply pulled back toward the face 23 rather than acting as an anchor toward which the main body of the endoscope is drawn as intended.

Also according to my invention, I provide means for positively fixing the pilot section relative to the passage through which the endoscope is to be moved. In FIG. 1 there is shown a detent frame 37 which defines supporting members 38 attached to slope surface 39 on which the endoscope rests. Brackets 40 and 41 hold the endoscope at a predetermined distance above the slope surface 39 and in slidable engagement therewith. The push ring 21 is connected to push cables 18 and completely encircles the endoscope. The pull ring 29, which is a semicircular ring, is connected to the pull cables 26 and placed a sufficient distance behind the push ring 21 such that they will not interfere with each other during their operation. Ridges 42 are provided on slope surface 39 to engage the push ring 21 and prevent it from moving backward during operation of the push and pull rings. These ridges 42 are defined by a series of peaks 43 and grooves 44 spaced equidistantly a distance which corresponds to the distance the pilot section 11 is to be extended beyound face 23 of the rigid portion. The brackets 40, 41 maintain a proper distance between the endoscope and the ridges 42 such that the push ring can be slid over peaks 43 to engage grooves 44 to prevent the backward movement of the push ring to the preceding groove. The pull ring 29 is semicircular and displaced from ridges 42 so that it will not engage the ridges 42 at any time during operation of the endoscope. With this frame structure the endoscope can be progressively moved forward without fear of its slipping back once the endoscope has been advanced.

As shown in FIG. 1, the patient is placed on a table and fixed relative to the detent frame so that the endoscope can be moved into the passage to the organ to be viewed. Once the distal end of the endoscope is initially inserted to some convenient distance by grasping the sheath 2 and simply moving it forward into the passage, it can then be operated from the proximal end by the push ring 21 and the pull ring 29 to advance the endoscope further into the passage. The push ring 21 is initially moved forward at least one notch on the ridges 42. This causes the pilot section 11 to move forward a corresponding distance from the face 23 of the endoscope. With the push ring seated in a notch the pilot section is effectively fixed relative to the passage. The pull ring 29 is then pulled back toward the proximal end of the endoscope. This causes that part of the cable between the face 23 and the pulley 30 to move forward and pull the main body of the endoscope along with it. It should be noted that when the push cables 18 are moved forward the pull ring 29 is pulled inwardly to a position from which it can be operated to pull the endoscope forward. Similarly, when the pull ring 29 is operated the endoscope tube will move relative to the push wires such that when the pulling operation is completed the push ring 21 will be in a position such that the pilot section 11 may be pushed forward by the distance of another notch. Repetition of this sequence of operation allows the endoscope to be inserted into the passage as far as the position of the rings on the flexible portion of the scope.

As shown in FIG. 1, push ring 21 is provided with a rod 45 threadably engaged through the push ring 21 and connected to a lever 46. The rod has sufficient length that it can be extended to engage the sheath 2 of the endoscope. With this mechanism, after the push ring 21 is moved to a groove 44, the lever 46 is simply turned to move the extension into engagement with the sheath 2. In this manner, a fine adjustment of the endoscope is obtained between the peaks 43 of ridge 42 for precisely locating distal end 3 relative to the site being viewed or operated on. The fine adjustment facilitates any biopsy or, extraction, or other operation as movement at the distal end would not have to be compensated which otherwise would be required. When it is desired to move the endoscope forward again the lever is turned back to its initial position withdrawing the extended rod from the sheath allowing the ring to pass over the next peak.

There is also incorporated on pull ring 29 a lever 47 which acts to fix pull ring 29 in a given position on the endoscope. The lever 47 includes a threaded shaft 48 threadably engaged through the top portion of the ring such that turning of the lever 47 will cause the end of the shaft to engage the endoscope surface to fix the ring relative to that surface. As with the extension mechanism the ability to fix the pull ring at a given position enhances the stability at the distal end of the endoscope. This mechanism can be disenegaged by simply moving the lever in the opposite direction.

Of the two brackets 40 and 41, the one closest to the proximal end is slidably secured to slope surface 39 by an under portion 49. A set screw 50 is threadably attached through under portion 49 and connected to lever 51. As the endoscope is moved progressively into the passage being viewed in bracket 41 can be disengaged and slid forward a sufficient distance to allow operation of the rings 21, 29. Continued operation of this merchanism will result in the bracket being moved ultimately to the end of the frame 37. This allows the endoscope to be inserted, if necessary, up to the rings 21, 29 at the proximal end.

The frame 37 is fixed slidably on a track 52 as shown in FIG. 1. The support members 38 of the frame 37 have wheels 53 which engage the upper surface of the track 52. The support members 38 carry a boss 38' above and proximate the track 52. A frame brake 54 is rotatably secured in this boss 38' for fixing the frame 37 relative to the track 52. A brake lever 55 extends at right angles from the brake 54 at the point where the brake 54 is rotatably attached to the boss 38'. As the brake is moved to the vertical position as shown in FIG. 1, it frictionally engages the track 52 and the wheels 53 are disengaged from the track to hold the frame in position. Movement of the brake into and out of engagement with the track 52 is accomplished by hand operation of lever 55. In this manner the entire frame 37 can be moved relative to the passage being viewed, and, if necessary, fixed in the desired position.

The pilot section 11 is configured to allow operation of the fiber bundles and other accessory devices unimpaired by the cables and pulleys used in advancing the endoscope. As shown in FIG. 6 the tubes for water 7, air 8 and biopsy 9 are open at the distal end face 23 at 31, 32 and 33 respectively. At the proximal end these tubes 7, 8, 9 are connected to control devices from which they can be operated remotely during the use of the endoscope. On the outer surface 14 of the pilot section 11 there are openings 34, 35 and 36 registered with the corresponding openings 31, 32 and 33 on the surface 23 of rigid portion 10. This provides a passage for the air, water or biopsy mechanism, when in operation, through the pilot section 11. Similarly, there are provided openings 5' and 6' in face 23 and 5" and 6" in end wall 12 to allow light to pass to fiber bundles 5 and 6. However, there is no provision for openings for the cables 26; thus, the outer surface 14 presents a smooth surface from which cables or other like devices do not protrude except for the openings through which light, air, water or a biopsy device can pass. This enhances the ability of the device to move forward into the passage smoothly without damaging the walls of that passage.

An alternate embodiment in FIGS. 7 and 8 shows a portable attachment 56 which can be used with a standard endoscope E. The attachment 56 is a flexible sheath 57 which has an open end 58 and a closed end 59. The open end 58 is unimpeded so that the sheath may be slipped over the standard endoscope. The closed end 59 is provided with a mechanism 60 for advancing the endoscope into the passage. Closed end 59 has a rigid portion 61 which is cylindrical in configuration and defines an annular cavity 62. A pilot section 63 is cylindrical in shape having side walls 64 and end wall 65. The side walls 64 are so dimensioned that they fit slidably into the annular cavity 62. The flexible sheath 57 has secured about the perimeter of its inner surface three push cable tubes 66 and three pull cable tubes 67 spaced equiangularly from each other and extending from one end of the sheath to the other. The tubes 66, 67 are open ended at both the ends of the sheath. This allows passage of push cables 68, and pull cables 69 through the tubes 66, 67 respectively. At the open end 58 of the sheath push cable tubes 66 emerge at the openings 70 on surface of sheath and similarly the pull cable tubes 67 emerge at openings 71 between the openings 70 and open end 58. As with the unitary structure, in the attachment 56 the cables 68, 69 are fixed to push ring 72 and pull ring 73 respectively. The openings 70, 71 for tubes 66, 67 are located relative to each other such that the rings will not interfere with one another during their operation.

The endoscope E has two fiber bundles, a large bundle 74 and a smaller bundle 75 and tubes 76, 77, 78 for utilizing respectively air, water, and a biopsy mechanism at the closed end 59. The bundles 74, 75 and tubes 76, 77, 78 emerge at face 79 of the endoscope E and extend back to a position remote from the closed end 59 where they can be utilized by an operator in the same manner as bundles 5, 6 and tubes 7, 8, 9 described with respect to the unitary device. The rigid portion 60 has an annular ring 80 which defines a circular opening 81. The end wall 65 of pilot section 63 also defines an opening 82 therethrough which is concentric with opening 81. These openings are sufficiently large that they allow operation of the bundles 74, 75 and tubes 76, 77, 78 unimpaired from the closed end 59.

Pulleys 83 are fixed rotatably to brackets 84 on the end wall 65 between opening 82 and side walls 64. The pull cables 69 extend through tubes 67, are reeved through pulleys 83, and are fixed to annular ring 80. The push cables 68 extend through the push tubes 66 and are fixed to end wall 65 spaced from pulleys 83 and between opening 82 and side walls 64. As with the unitary structure each push cable 68 has a rigid portion 85 which is approximately the same length as rigid portion 60 of sheath 54. Alternate movement of the push ring 72 and pull ring 73 will cause pilot section 63 to move relative to rigid portion 60 in the same manner as described in connection with the unitary structure to progressively move the endoscope into the passage being viewed.

On the exterior surface of the sheath 57 at a given cross-section there are three countersunk holes 86, a portion of which are of threaded at 87, at several locations along the length of the sheath. Threadedly engaged with these holes are set screws 88 which are of a sufficient length to extend beyond the inner surface 89 of the sheath to contact the outer surface of the endoscope such that head 90 of the set screw 88 does not extend beyond the outer surface of the sheath. With this configuration the sheath can be slid over the endoscope and the set screws 88 tightened to fix the attachment 56 with respect to the endoscope. With the holes being countersunk there is provided a smooth outer surface on the sheath so that the passage will not be damaged during movement of the endoscope.

The push ring 72 and pull ring 73 each incorporate a threaded rod 91, 92 connected respectively to levers 93, 94. The rods 91, 92 are similar to the rods 45, 48 as discussed with respect to the unitary device and operate in the same manner to fix the distal end relative to the organ being viewed.

The advantages of such an attachable and detachable device described with respect to FIGS. 7 and 8 are that it can be used with a standard endoscope without forcing the operator to purchase an entire unit when he already has the basic device. In addition there may be occasions where the mechanism for advancing the endoscope is not needed in which case the attachment may be simply slid from the endoscope after the set screws have been sufficiently loosened.

Another embodiment is shown in FIGS. 9, 10, 11 and 11a where a standard endoscope 95 is covered with a sheath 96 having an advancing mechanism 97 at the distal end thereof. As shown, the distal terminal portions of push cables 98 are rendered rigid by being covered with tubes 100 of rigid material. These tubes extend from inner surface 101 of pilot ring 99 to a proximal point at which they will still be within sheath 96 when mechanism 97 is fully advanced. This length provides support for the pilot ring 99 in the extended position, Extending rearwardly from advancing ring 99 is guard 102 with a pulley 103 rotatably attached to the guard's inner surface. Reeved through the pulley 103 is the pull cable 104, one end of which is fixed to the end 105 of sheath 96 and the other end of which is fixed to a pull ring at the proximal end of the endoscope.

Figure 9:
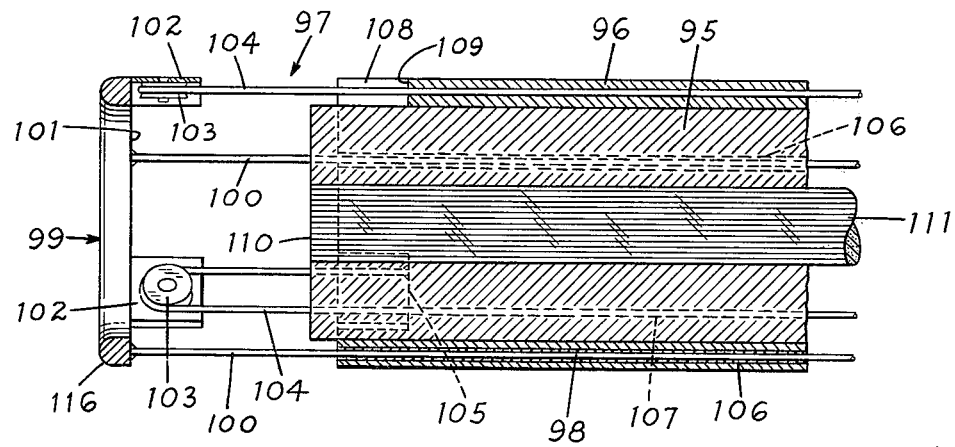
FIG. 9 shows a cross section of another embodiment of an endoscope at the distal end.

The portion of the sheath shown in FIG. 9 is entirely rigid with passages 106, 107 to allow passage of the push cables 98 and pull cables 104 respectively. The remainder of the sheath, not shown, is flexible and extends to the proximal end of the endoscope as with FIGS. 1-8. To advance the endoscope, the pilot ring 99 is moved relative to the endoscope in the same manner as the pilot sections 11, 63 described in connection with FIGS. 1-8 and need not be reiterated here. The embodiment shown in FIGS. 9, 10, 11 and 11a shows the sheath permanently secured to the surface of the endoscope to form a unitary device. However, this advancing mechanism can also have its sheath detachably secured in the manner described with respect to FIG. 7.

Figure 10:
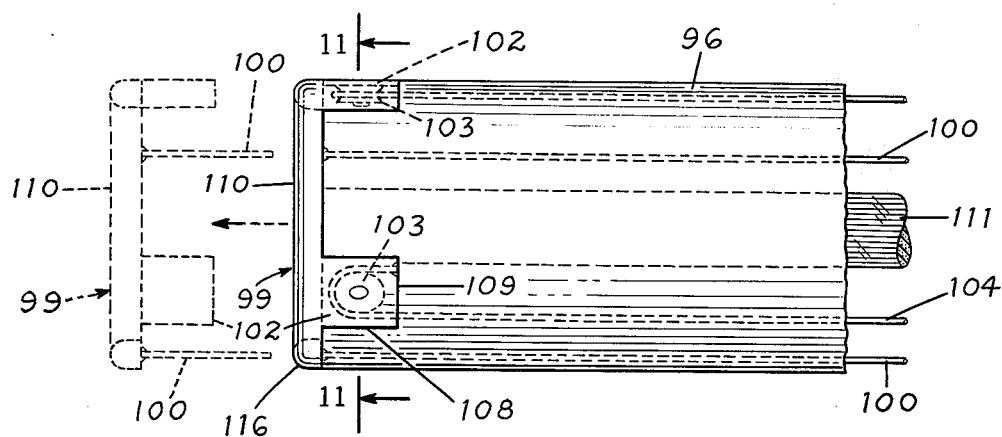
FIG. 10 is an elevation of the device shown in FIG. 9 with the advancing mechanism shown in the closed position.

The combined width of the guard 102 and pulley 103 is slightly less than the thickness of sheath 96. As best seen in FIG. 11a, the sheath end 105 defines a slot 108 to receive the guard 102 in the closed position. The slot 108 has a slot bottom 109 from which the pull cables emerge through passages 107 and to which are attached the ends of pull cables 104. Similar to the embodiments described in FIGS. 1-8, the endoscope in FIG. 11 has an endoscope face 110 with fiber bundles 111, 112 and tubes 113, 114, 115 emerging at the endoscope face for viewing and operating in the area being viewed. The sheath end 105 is displaced from the endoscope face 110 of the endoscope a distance equal to the thickness of pilot ring 99, as measured in the direction of the ring movement relative to the face 110 of the endoscope. The location of the sheath end 105 and the configuration of slot 108 allow the outer surface of the pilot ring to be moved in the closed position to the same plane as that of the endoscope face 110 as shown in FIG. 10. By withdrawing the pilot ring 99 to this position the entire face 110 of the endoscope is exposed to provide clear viewing and unimpeded operation of the other elements of the endoscope. The outer surface of the pilot ring 99 and guard 102 coincide with the same plane as the outer surface of the sheath 96. This coincidence provides a smooth outer surface when the pilot ring 99 is in the closed position. Also, the pilot ring has an outer surface 116 which is rounded so that forward movement of the pilot ring 99 will not damage the passage being viewed.

Figure 11:
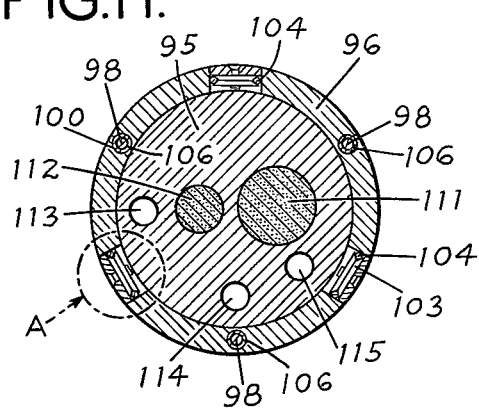
FIG. 11 is a cross section of the device shown in FIG. 10 along lines 11—11.
Figure 11A:
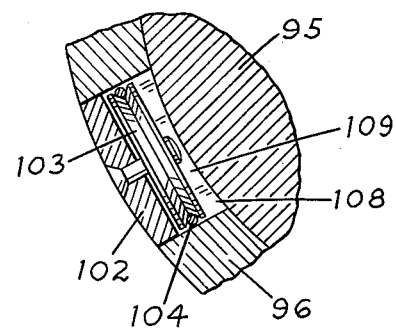
FIG. 11a is the portion at "A" of FIG. 11 blown up to more clearly show the interaction of the pulley with other elements of the advancing mechanism.

As shown in FIG. 11 there are provided three pulleys 103 and their accompanying cables 104 and three push cables 100 spaced equiangularly around the sheath. By having the advancing mechanism wholly within the sheath and the pilot ring 99 fully retractable, this mechanism does not interfere with other features of a standard endoscope while adding to it the ability to be moved deep into the passage being viewed without discomfort to the patient. Further, with the use of rigid push tubes 100 on the push cables 98 the need for an annular structure to support the pilot ring 99 is eliminated. Because of the simplicity of structure as discussed with respect to FIGS. 9, 10, 11 and 11a, lower manufacturing costs are achieved without loss in efficiency of operation.

The accompanying drawings do not show a mechanism for bending the endoscope to guide it through a tortuous path. An example of such a mechanism is shown in the U.S. Pat. to Richards, No. 3,091,235. This mechanism may form part of the preferred embodiments as discussed above. The other elements of the endoscope including the push and pull cables, the biopsy tube, the air and water tubes and the fiber bundles are located so as not to interfere with the mechanism for bending the endoscope. These details are not shown in the drawings as one skilled in art can readily incorporate the elements disclosed in the Richards patent into the device shown in FIGS. 1–11 without further elaboration.

Whether the device is an attachment which can be secured to a standard endoscope or it is a unitary structure, it enables the operator to remotely advance the scope into passages which heretofore could not be readily achieved. The operator can, by remote control, move the push and pull rings to progressively advance the distal end of the scope into the passage. This insures advancement without unnecessary bending of the portion of the endoscope between the proximal end and the distal end. By advancing the endoscope in this manner much discomfort for the patient which heretofore existed is substantially eliminated. Further, the device described herein is one which is economical to manufacture and simple and efficient in operation while facilitating maximum use of the other elements of the endoscope.

I claim:

1. An endoscope having a distal end and a proximal end for viewing remote areas by transferring an image from the distal end where the object for viewing is located to the proximal end where the image transferred can be viewed by an operator comprising:

1. a flexible fiber optical bundle comprised of light conducting fibers,
    2. at least a portion of the fiber optical bundle being arranged at the distal end to define an optical face for receiving an image and transferring that image to the proximal end of the endoscope,
    3. means at the proximal end of the endoscope for viewing the image transferred from the face of the distal end, and
    4. moving means at said distal end operable from the proximal end for tractively advancing the endoscope progressively into a passage, said moving means including a small rigid portion fixedly attached at the distal end, a movable pilot section which is slidably engaged with the rigid portion of the distal end, and said moving means further includes means for moving the pilot section relative to the rigid portion and alternately moving the rigid portion relative to the pilot section such that the distal end of the endoscope can be tractively advanced into a passage.

2. The endoscope according to claim 1 wherein said means for moving the pilot section includes push cables with one end of each cable attached to the pilot section and the other end of each cable attached to control means at the proximal end of the endoscope for remote control by an operator, and said means for moving the rigid portion of the distal end includes pull cables each having one end secured to control means at the proximal end of the endoscope for remote control by an operator, the other end cooperating with direction reversing means and connected to said rigid portion of the distal end.

3. The endoscope according to claim 2, further comprising tubes extending from the distal end to the proximal end of the endoscope, said tubes providing means through which, including but not limited to, a biopsy mechanism, air and water can pass, an endoscope face at the distal end of the endoscope through which the fiber bundle and tubes emerge, bending means for bending the endoscope adjacent the distal and operable from the proximal end, wherein said moving means is operable without substantially affecting operation of said tubes and said bending means.

4. The endoscope according to claim 3 wherein the means for reversing direction includes a pulley rotatably attached to said pilot section and said pull cable being reeved through said pulley.

5. The endoscope according to claim 4 wherein the rigid portion of the distal end is cylindrical in configuration and defines a longitudinally extending annular cavity coaxial with it and near its outer perimeter, and the pilot section is also cylindrical in configuration with side walls and an end wall, said sidewalls configured for slidable engagement with said annular cavity defined by the rigid portion of the distal end, said end wall having an outer surface and an inner surface, the pulleys being rotatably attached to said inner surface.

6. The endoscope according to claim 5 wherein said push cable defines a rigid cable portion at the distal end of the endoscope substantially the same length as the rigid portion and fixedly secured to the inner surface of the end wall of the pilot section.

7. The endoscope according to claim 6 wherein a sheath of flexible material circumscribes the fiber optical bundle along substantially its entire length, said sheath containing three tubes for slidably carrying the push cables and three tubes for slidably carrying the pull cables along their longitudinal axes such that these cables can move relative the tube along their longitudinal axes regardless of the configuration of said endoscope, these tubes are fixed at the distal end of the endoscope and emerge at openings through the face of the rigid portion at said distal end, said tubes also being fixed at the proximal end of the endoscope and extending through the sheath, the cables being of sufficient length for moving the pilot section and the rigid portion at the distal end and always having a portion of the cables extending through the openings defined in the sheath at the proximal end of the endoscope for use by an operator.

8. The endoscope according to claim 7 further comprising operating means connected to said cables at the proximal end of the endoscope enabling said cables to be manually operated at said proximal end.

9. The endoscope according to claim 8 further comprising a detent frame on which said sheath is slidably secured, said operating means including a push ring attached to the push cables and a pull ring attached to the pull cables, said rings being slidably secured to the sheath, said detent frame defining restraining means cooperating with said rings to prevent the endoscope from sliding back after said push ring has been moved in the direction of said distal end.

10. The endoscope according to claim 9 wherein said restraining means includes restraining ridges cooperating with said push ring such that when the push ring is moved forward a sufficient distance it will slide into the next adjacent restraining ridge preventing it from moving backward to the position from which it started without affecting movement of the pull ring.

11. The endoscope according to claim 9 wherein the detent frame is slidably secured on a track and said detent frame further comprises a lock means for locking the frame on the track at a desired location.

12. The endoscope according to claim 1 wherein said moving means includes pilot ring and rigid tubes fixedly attached to said pilot ring, said rigid portion defining passages therein for slidably engaging said rigid tubes, and said rigid tubes being of sufficient length for supporting the pilot ring during movement of the pilot ring relative to the rigid portion.

13. The endoscope according to claim 12 wherein said endoscope includes means for bending the endoscope adjacent the distal end and operable from the proximal end, tubes extending from the distal end to the proximal end of the endoscope, said tubes providing means through which, including but not limited to, a biopsy mechanism, air and water can pass, an endoscope face at the distal end of the endoscope through which the fiber optical bundle and tubes emerge, and the pilot ring having an effective diameter at least slightly greater than that of the endoscope for exposing said endoscope face for allowing operation of the fiber optical bundle and the tubes unimpeded by the moving means.

14. The endoscope according to claim 13 wherein said moving means includes push cables with one end of each push cable attached to said pilot ring and the other end of each push cable attached to control means at the proximal end of the endoscope for remote control by an operator and pull cables having one end secured to the control means at the proximal end of the endoscope for remote control by an operator, the other end cooperating with direction reversing means and connected to the rigid portion.

15. The endoscope according to claim 14 wherein the means for reversing direction includes a pulley rotatably attached to the pilot ring and said pull cable being reeved through said pulley.

16. The endoscope according to claim 15 wherein the rigid portion includes a sheath circumscribing the endoscope about the endoscope's outer perimeter, and said sheath defining the passages through which the push cables move during operation moving means, said rigid tubes being clamped to the push cables and said passages for the push cables also providing for movement of the rigid tubes as well as the push cables.

17. The endoscope according to claim 16 wherein the pilot ring has a portion extending rearwardly, said portion defining an inner and outer surface, the pulley being attached to the inner surface of said portion.

18. The endoscope according to claim 17 wherein the sheath defines a sheath end displaced rearwardly from the face of the endoscope a distance which corresponds to the thickness of the ring, the sheath further defines a slot for receiving the extended portion of the pilot ring, the sheath end and the slot cooperating with the pilot ring and the extension for allowing the pilot ring to be moved in a closed position to substantially the same plane as that defined by the face of the endoscope.

19. The endoscope according to claim 18 wherein the extended portion defines a guard having a width and length greater than the diameter of the pulley for covering the pulley, said pulley said guard having a combined thickness less than the thickness of the sheath for moving the guard and pulley into and out of the slot defined by the sheath.

20. The endoscope according to claim 19 wherein the outer surface of the pilot ring and guard coincide with the plane defined by the outer surface of the sheath such that in the closed position a continuous smooth outer surface is presented.

21. The endoscope according to claim 20 wherein the slot defines a slot bottom to which the end of the pull cable is attached.

22. The endoscope according to claim 21 wherein the sheath defines three slots, the pilot ring defines three guards each having a pulley rotatably attached thereto, and three push cables are each fixed to a rigid tube which in turn is connected to the pilot ring, three pull cables each of which are reeved through a respective pulley and connected to the slot bottom of the slot in the sheath, and said guards registering with the slots such that as the pilot ring is moved into the closed position it will be sufficiently displaced from the endoscope face to allow operation of the fiber optical bundle and the operating tubes unimpeded by the moving means.

23. For use with an endoscope having a flexible optical fiber bundle comprised of light conducting fibers, a portable attachment having means for securing the endoscope to said attachment, said attachment having a distal end and a proximal end and means at its distal end for advancing the attached endoscope into the passage desired to be viewed, said attachment having remote control means at its proximal end for remotely operating said advancing means at the distal end.

24. The attachment according to claim 23 wherein said attachment is an elongated flexible tube having an open end at said proximal end and a closed end at said distal end, said open end being sufficiently large to slide over the endoscope, said closed end having said advancing means for progressively advancing said endoscope into a passage.

25. The attachment according to claim 24 wherein said closed end of said attachment defines a rigid portion when fits over said endoscope and a pilot section which slidably engages the rigid portion such that it can move relative thereto, said rigid portion and said pilot section cooperating to progressively advance the endoscope into the passage to be viewed when actuated by said remote control means.

26. The attachment according to claim 25 wherein said means for remotely controlling the rigid portion and the pilot section comprises push cables which extend the entire length of the sheath and are at the closed end connected to said pilot section and at the open end extended outwardly from the sheath for use by an operator, and pull cables extending the entire length of the sheath and are at the closed end attached to the rigid portion and at the open end extended out of the sheath for use by an operator, said pull cables cooperating with direction reversing means at the closed end of said attachment to enable pulling forces on said pull cables at the proximal end to be transformed into forces which pull the rigid portion of the attachment toward the pilot section which in turn pulls the entire endoscope toward the pilot section.

27. The attachment according to claim 26 wherein the attachment defines along its inner periphery tubes through which push cables and pull cables can move relative thereto, said tubes being fixed at both ends of the attachment, at the closed end of the attachment said tubes defining an opening adjacent the rigid portion of the attachment, at the proximal end of the sheath said tubes emerge at an opening defined in an outer surface of the attachment, the cables having a length greater than that of said tubes for always providing a sufficient length of cable extending out from the openings defined in the surface of the attachment for control by an operator.

28. An attachment according to claim 27 wherein the means for reversing direction includes a pulley rotatably attached to said pilot section and said pull cable being reeved through said pulley.

29. The attachment according to claim 28 wherein the rigid portion is cylindrical in configuration and defines an annular cavity near its outer perimeter, said pilot section also being cylindrical in configuration and defining side walls and an end wall, said pilot section having said sidewalls configured for slidable engagement with the annular cavity defined by the rigid portion of the closed end, said end wall having an upper surface and an undersurface, said pulleys being rotatably attached to said undersurface.

30. The attachment according to claim 29 wherein said push cable defines a rigid cable portion at the closed end of the endoscope substantially the same length as the rigid portion and fixedly secured to the undersurface of the pilot section.

31. The attachment according to claim 30 wherein said remote control means includes operating means connected to said cables at the proximal end, for manually operating said cables.

32. The attachment according to claim 31 wherein said operating means includes a push ring attached to the push cables and a pull ring attached to the pull cables, said rings being slidably secured to the attachment, and restraining means cooperating with said rings to prevent the endoscope from sliding back after push ring has been moved in the direction of said distal end.

33. The endoscope according to claim 32 further comprising lever means threadably engaged with said rings for fixing said rings relative to the attachment.

* * * * *